United States Patent [19]
MacKay et al.

[11] Patent Number: 5,770,381
[45] Date of Patent: Jun. 23, 1998

[54] METHODS FOR THE DIAGNOSIS OF DIABETES AND PREDIABETIC CONDITIONS

[75] Inventors: Ian Reay MacKay, Malvern; Merrill Joy Rowley, Camberwell; Paul Zev Zimmet, Toorak, all of Australia

[73] Assignee: Monash University, Clayton, Australia

[21] Appl. No.: 495,584

[22] PCT Filed: Feb. 9, 1994

[86] PCT No.: PCT/AU94/00056

§ 371 Date: Oct. 10, 1995

§ 102(e) Date: Oct. 10, 1995

[87] PCT Pub. No.: WO94/18568

PCT Pub. Date: Aug. 18, 1994

[30] Foreign Application Priority Data

Feb. 9, 1993 [AU] Australia .................................. PL7168

[51] Int. Cl.$^6$ .................................................. G01N 33/53
[52] U.S. Cl. .............................. 435/7.1; 435/7.4; 435/232
[58] Field of Search ................................ 435/232, 7.1, 4, 435/7.4; 424/94.5

[56] References Cited

FOREIGN PATENT DOCUMENTS

92/05446  4/1992  WIPO.
92/14485  9/1992  WIPO.
92/19972  11/1992  WIPO.

OTHER PUBLICATIONS

Biochemistry—USSR (Abstract Only), Darii et al. vol. 57, No. 4, Apr. 1992, pp. 393–399.
D. L. Kaufman et al., "Autoimmunity to Two Forms of Glutamate Decarboxylase in Insulin–dependent Diabetes Mellitus", J. Clin. Invest., vol. 89, Jan. (1992), pp. 283–292.
Baekkeskov et al."Identification of the 64 K autoantigen in insulin–dependent diabetes as the GABA–synthesizing enzyme glutamic acid decarboxylase," Nature 347:151–56 (1990).
Rowley et al."Antibodies to Glutamic Acid Decarboxylase Discriminate Major Types of Diabetes Mellitus," Diabetes 41:548–51 (1992).
Karlsen et al."Cloning and Primary Structure of a Human Islet Isoform of Glutamic Acid Decarboxylates from Chromosome 10," Proc. Natl. Acad. Sci. USA 88:8837–41 (1991).
Michelson et al."Cloning, Characterization, and Autoimmune Recognition of Rat Islet Glutamic Acid Decarboxylase in Insulin–Dependent Diabetes Mellitus," Proc. Natl. Acad. Sci. USA 88:8754–58 (1991).
Kaufman et al."Brain Glutamate Decarboxylase Cloned in ygt–11: Fusion Protein Produces γ–Aminobutyric Acid," Science 232:1138–40 (1986).
Chang et al."Characterization of the Proteins Purified with Monoclonal Antibodies to Glutamic Acid Decarboxylase," Jour. Neurosci. 8(6):2123–30 (1988).
Nathan et al."A Membrane Form of Brain L–Glutanate Decarboxylase: Identification Isolation, and its Relation to Insulin–Dependent Diabetes Mellitus," Proc. Natl. Acad. Sci. USA 91:242–46 (1994).
Petersen et al."Characterization of the Oligomerization of Glutamate Decarboxylase have distinct Intraneuronal Distributions," Diabetes 41:38A (1992) Abstract No. 148.
Kaufmann et al."Two forms of the γ–Aminobutyric Acid Synthetic Enzyme Glutamate Decarboxylase Have Distinct Intraneuronal Distributions and Cofactor Interactions," Jour. Neurochem. 56:720–23 (1991).
Tuomi et al."Autoantigenic Properties of Native and Denatured Glutamic Acid Decarboxylase: Evidence for a Conformational Epitope," Clin. Immunol. Immunopathol. 71(1):53–59 (1994).
Tuck et al."Failure to Detect Antoantibodies Specific for IDDM by Western Blotting," Autoimmunity 13:173–74 (1992).
Karlsen et al."Recombinant Glutamic Acid Decarboxylase (Representing the Single Isoform Expressed in Human Islets) Detects IDDM–associated 64,000–$M_r$, Autoantibodies," Diabetes 41:1355–59 (1992).
Deaizpurua, et al."An ELISA for Antibodies to Recombinant Glutamic Acid Decarboxylase in IDDM," Diabetes 41:1182–87 (1992).
Schmidli et al."High Level of Concordance Between Assays for Glutamic Acid Decarboxylase Antibodies," Diabetes 43:1005–09 (1994).
Seissler et al."Prevalence of Autoantibodies to the 65– and 67–kD Isoforms of Glutamate Decarboxylase in Insulin–Dependent Diabetes Mellitus," J. Clin. Invest. 92:1394–99 (1993).
Hagopian et al."Autoantibodies in IDDM Primarily Recognize the 65,000–$M_r$, rather than the 67,000–$M_r$, isoform of Glutamic Acid Decarboxylase," Diabetes 42:631–36 (1993).
Kaufman et al."Glutamate decarboxylases and autoimmunity in insulin–dependent diabetes," Tips 107–09 (1993).

Primary Examiner—Keith D. Hendricks
Attorney, Agent, or Firm—Foley & Lardner

[57] ABSTRACT

A method for detecting autoantibodies to glutamic acid decarboxylase (GAD) in the serum of a patient as diagnostic of a diabetic or prediabetic condition in the patient, comprises contacting a serum sample from the patient with a GAD antigen and detecting binding of autoantibodies to GAD in the sample by the GAD antigen, wherein the GAD antigen comprises a GAD preparation containing an enhanced amount of dimer(s) or oligomer(s) of the 65 kD or 67 kD isoforms, or both, of GAD. A diagnostic kit is also inclosed.

21 Claims, 3 Drawing Sheets

METHODS FOR THE DIAGNOSIS OF DIABETES AND PREDIABETIC CONDITIONS

This Application is a 371 of PCT/AU94/00056, filed Feb. 9, 1994.

FIELD OF THE INVENTION

This invention relates to methods for the identification of persons who have diabetes or a prediabetic status, and in particular it is directed to a diagnostic assay which will provide a simple and effective means of screening large populations of individuals to detect both diabetes and pre-diabetes (the early stages of diabetes prior to the onset of the clinical disease).

BACKGROUND OF THE INVENTION

Diabetes mellitus is a heterogeneous disorder. Insulin-dependent (IDDM) and non-insulin-dependent diabetes mellitus (NIDDM) are subtyped physiologically according to patients' dependence for survival on treatment with insulin[1]. IDDM is attributed to autoimmunity[2] by reason of disease associations, autoantibodies to pancreatic islet cell antigens, similarities with animal models of IDDM and HLA linkages. The disease-relevant autoantigen or antigens in IDDM include a 64,000-$M_r$ protein demonstrable by immunoprecipitation from pancreatic islets[3] but hitherto unidentified because of low abundance and assay difficulties. Immunoassay for antibody to the 64,000-$M_r$ antigen indicated that it was a specific marker for IDDM and preceded symptomatic onset of disease[4]. The recognition in cases of the Stiff Man syndrome of coexisting IDDM and a neural antigen of 64,000–65,000-$M_r$ identified as glutamic acid decarboxylase (GAD) led Baekkeskov et al.[5] to establish the coidentity of their 64,000-$M_r$ antigen and GAD. Recently, Rowley et al.[6] described a high frequency of positive results by radioimmunoprecipitation assay with IDDM sera and a GAD preparation from pig brain and proposed detection of antibodies to GAD as a useful diagnostic test as an autoimmune marker associated with IDDM.

Insulin-dependent diabetes mellitus is a frequently occurring disease that predominantly affects young individuals, less than age 15 years. The disease can, however, have an onset in early or even mid-adult life, hence there is a need for a test that has diagnostic and predictive capacity for IDDM in both childhood and in adult life. The disease itself, IDDM, occurs at highest frequencies in the developed and economically advanced communities in the world. There is a high incentive to diagnose IDDM at the earliest stage, and even in the preclinical stage before the disease can be recognised by conventional laboratory tests. The recognition of antibodies to GAD by a routinely applicable, sensitive and specific immunoassay kit would fulfil this need. Moreover, the need for early or preclinical recognition is heightened by the likelihood that specific immunotherapeutic procedures will be developed that will arrest the progress of islet cell destruction that underlies IDDM, noting that such procedures have already been applied successfully in a model in mice of IDDM. Arrest of the natural progression of IDDM could spare patients years of injections with insulin. The development and application of an efficient immunoassay for antibodies to GAD, as a diagnostic procedure for IDDM, would result in an estimated usage of an assay kit in numbers exceeding one million annually, worldwide.

Apart from this, 5–10% of adults presenting with diabetes are initially diagnosed as having the non-insulin dependent form (NIDDM), however, after aL period ranging from months to years, they convert to IDDM. These patients fall into a category called latent autoimmune diabetes in adults (LADA). It has been shown that 75–80% of this group of patients have detectable levels of antibodies, to GAD. It is likely that this test will become widely used to discriminate these patients at diagnosis, thus saving them from inappropriate therapy (i.e. diet and tablets) which could result in failure to control their diabetes with the subsequent risk of severe complications. Moreover, the test for antibodies to GAD could have predictive value if applied to individuals at risk by reason of genetic predisposition. The institution of insulin therapy at an early stage, based on the demonstration of antibodies to GAD would avert this scenario.

The onset of IDDM is preceded by a clinically silent destruction of the pancreatic β-cells usually by an autoimmune process [2,7] serologically associated with autoantibodies to islet cell antibodies (ICAs). These include the 64,000-$M_r$ protein, now recognised as GAD[3,4], the cytoplasmic ICA demonstrable by immunofluorescence[8] and insulin autoantibodies[9]. Antibody to the 64,000-$M_r$ molecule has been extremely difficult to assay because of the need to prepare antigen from large quantities of islet cell preparations. However, Rowley et al.[6] showed that with radioiodine-labelled GAD prepared from pig brain, the antibody could be readily and specifically detected by an immunoprecipitation assay. It is of interest that the 64,000-$M_r$ antigen is an enzyme molecule as are various other disease-relevant autoantigens, most notably thyroid peroxidase in autoimmune thyroid[14], $H^+K^+$ ATPase in autoimmune gastritis[11], and pyruvate dehydrogenase in primary biliary cirrhosis[12]. GAD is not species specific and, in fact, cDNAs for brain GAD from humans[13], rat[14], and cat[15] have such close homology that antibody reactivity could be expected with any mammalian GAD preparation. Also, the autoantigen is clearly not organ specific because the source used by Rowley et al.[6] was brain. The sequence of GAD from brain and pancreatic islets, the major sites in which GAD is demonstrable, appears to differ only by allelic variations[16,17]. GAD exists as at least two isoforms[18], and the Rowley et al.[6] preparation contained both representatives, as indicated by data by polyacrylamide gel electrophoresis (PAGE).

GAD synthesises γ-aminobutyric acid (GABA), the principal inhibitory neurotransmitter in the brain and a putative paracrine signal molecule in pancreatic islets. The enzyme has a restricted tissue distribution and is highly expressed in the cytoplasm of GABA-secreting neurons and pancreatic β-cells. The two isoforms of GAD are referred to as GAD 65 and GAD 67 according to their relative molecular masses. These isoforms are the products of two different genes and differ substantially only in their amino-terminal region.

In addition, GAD appears to exist as an integral membrane protein with hydrophobic properties, and is present as a non-covalently linked dimer of MW 96,600[20]. This purified membrane form of GAD has been found to be reactive with IDDM sera, however no sequence data are yet available for this integral membrane protein[20].

The development of simple assays for anti-GAD will provide a valuable tool for diabetes research, particularly as anti-GAD is not a transient reactivity, unlike the sensitivity to the pancreatic islet cytoplasmic antigen. Numerous studies affirm not only that the frequency of anti-GAD is high in IDDM, and in cases of recent onset approaches 70–80%, but also the stability of anti-GAD levels over a period of years[6]. In fact, even among cases of very long-standing IDDM, the frequency of anti-GAD remains high, at about 60%[21].

Research has also shown that autoantibodies to GAD appear in the bloodstream long before the clinical symptoms of diabetes actually occur[4]. In a study by the present inventors on individuals selected as being at risk for IDDM by reason of inheritance and positive for antibodies to β-islet cells of the pancreas showed that the presence of anti-GAD in serum correlated strongly with later appearance of IDDM[22]. In further studies by the present inventors, anti-GAD has been present in the first available serum sample from 80% of prediabetic individuals, and even 10 years before the overt onset of diabetes[23]. Because it is present years before the onset of diabetes, the GAD autoantibody is a valuable predictive marker of the disease, and in a study in Finland[23] based on serum samples obtained from apparently healthy pregnant women who subsequently developed IDDM, the predictive capacity for IDDM of a positive test for anti-GAD was remarkably high a relative risk versus a negative test for anti-GAD being 800-fold. In Melbourne, a study on stored sera from women with gestational diabetes (diabetes appearing during pregnancy) likewise showed that a positive test for anti-GAD was predictive of the occurrence later in life of IDDM in such women[24].

International Patent Specification No. PCT/US91/06438 (Publication No. WO 92/04632) discloses assays for the detection of diabetes or a prediabetic status relying on exposing patient serum samples to purified ligand capable of binding autoantibodies specific for the 64 kD autoantigen present on pancreatic β-cells.

Research work leading to the present invention has now identified the molecular form in which GAD functions as an antigen, and hence binds efficiently and effectively to autoantibodies in an immunoassay for diabetes or the preclinical stage of diabetes. It is now evident that the monomeric form of GAD is, with rare exceptions, a poorly reactive antigen for IDDM sera, and for an effective assay to demonstrate the reactivity with GAD, the preparation must contain a proportion of GAD in the dimeric or oligomeric configuration. As a result, it is now possible to optimise the form of the antigen used in the detection of autoantibodies to GAD, leading to increased sensitivity in assays for the detection of diabetes or a prediabetic status.

SUMMARY OF THE INVENTION.

In accordance with the present invention there is provided a method for detecting autoantibodies to glutamic acid decarboxylase (GAD) in the serum of a patient, comprising contacting a serum sample from the patient with a GAD antigen and detecting binding of autoantibodies to GAD in said sample by said GAD antigen, characterised in that said GAD antigen comprises a GAD preparation containing an enhanced amount of dimer(s) or oligomer(s) of the 65 kD and/or 67 kD isoforms of GAD.

Whilst the present description of the invention refers specifically to detection of antibodies to GAD in a serum sample, it is to be understood that the term "serum" is used as a non-limiting term, and that the present invention also extends to the detection of autoantibodies to GAD in "blood" samples in general, including blood serum and plasma.

As a particularly preferred feature of the present invention, the method of the invention is carried out under conditions under which the dimeric or oligomeric form of the GAD is retained and is not broken down into monomeric GAD. Preferably, therefore, the method of the invention is carried out under non-denaturing conditions, and particularly under non-reducing conditions.

It will, of course, be appreciated that the detection of binding between the autoantibodies and the GAD antigen is indicative of the presence of the autoantibodies in the serum sample, and hence is diagnostic of a diabetic or prediabetic condition in the patient.

In yet another embodiment, the present invention provides a non-naturally occurring preparation of GAD antigen which contains an enhanced amount of dimer(s) or oligomer(s) of the 65 kD and/or 67 kD isoforms of GAD.

The present invention further extends to a diagnostic kit for the detection of autoantibodies to GAD in the serum of a patient, comprising a GAD antigen and means for detecting binding of autoantibodies to GAD in a serum sample from the patient by said GAD antigen, characterised in that said GAD antigen comprises a GAD preparation containing an enhanced amount of dimer(s) or oligomer(s) of the 65 kD and/or 67 kD isoforms of GAD.

The references herein to an "enhanced amount" of dimer(s) or oligomer(s) in the GAD preparation indicate that the amount of dimer(s) or oligomer(s) in the GAD preparation is greater than the amount of dimer(s) or oligomer(s) in preparations of naturally occurring GAD. Such greater amounts may be achieved by separation of naturally occurring GAD into fractions having an "enhanced amount" of dimer(s) or oligomer(s), for example by electrophoretic separation on SDS-PAGE gels or by size exclusion chromatography. Alternatively, such an "enhanced amount" of dimer(s) or oligomer(s) may be achieved by augmenting the content of dimeric or oligomeric GAD in naturally occurring GAD.

It should also be noted that the references herein to GAD preparations having an enhanced amount of dimer(s) or oligomer(s) also include preparations of "substantially pure" GAD having greater than 50% by weight, more particularly greater than 70% by weight or even greater than 90% by weight, of the dimeric or oligomeric form of GAD, with the balance monomeric GAD. Such "substantially pure" dimeric or oligomeric GAD may be produced by removal of appropriate amounts of monomeric GAD from naturally occurring GAD using known separation techniques. Alternatively, however, the dimeric or oligomeric GAD may be synthesised by appropriate cross-linking, for example by forming disulphide bonds or by other means, of naturally occurring or recombinantly produced monomeric GAD.

Accordingly, in one particular aspect, the present invention provides a GAD preparation which comprises substantially pure dimer(s) or oligomer(s) of the 65 kD and/or 67 kD isoforms of GAD, and in particular a GAD preparation which comprises substantially pure heterodimer or heterooligomer of the 65 kD and 67 kD isoforms of GAD.

The dimer(s) or oligomer(s) in the GAD preparation used as antigen in this invention may be an aggregation of one or other of the two isoforms of GAD, or it may be a heterodimer or heterooligomer of both isoforms (65 kD or 67 kD) of GAD. Similarly, the GAD may be either human or non-human mammalian, natives or recombinant, and it may be either pancreatic or brain (or other CNS) GAD.

Methods for the isolation of native GAD are well known, and are described, for example, in International Patent Specification No. PCT/US91/06438 (WO 92/04632). This International specification also describes various methods for the preparation of recombinant GAD. The disclosure of all these methods is incorporated herein by reference.

Throughout this specification and claims which follow, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION.

The GAD preparation used in the work leading to the present invention was obtained from porcine brain and was purified as described in Rowley et al.[6] on an affinity column that contained a monoclonal antibody GAD1 reactive with mammalian GAD[19]. This preparation contained predominantly monomeric GAD (65 kD and 67 kD) but also contained some dimeric and oligomeric GAD. As described above, this preparation may be further processed to provide a preparation containing an enhanced amount of dimeric or oligomeric GAD, for example, by electrophoretic separation.

When GAD is isolated from natural sources, the major component is monomeric GAD which is not cross-linked. In the work leading to this invention, it was discovered that it is the minor dimeric/oligomeric fraction in such naturally occurring GAD which proves to be the "antigenic" component. Therefore, in order to effectively bind with the autoantibodies present in the sera of diabetic or prediabetic patients, the GAD must exist in the dimeric or oligomeric form, and it has been found that for most diabetic sera there is little or no reactivity with monomeric GAD. This discovery was both unanticipated and unpredictable.

Using a procedure of molecular separation of GAD in gels under non-denaturing conditions which preserve the native conformation of the molecule, it has been shown that the molecular weight of the GAD molecule that binds to the autoantibody in IDDM is almost exactly double that of the monomeric form of the GAD molecule, hitherto believed to be the "diabetes autoantigen". It is emphasised that for almost all the diabetic sera tested so far, little or no monomer is bound by the autoantibody, even in the presence of a 20-fold or greater excess of the monomeric GAD. It therefore follows that the dimeric configuration of the GAD molecule presents an optimal antigen determinant for the autoantibody reaction. In addition, it is evident that any procedure that augments the amount of dimeric GAD vis-a-vis monomeric GAD will increase greatly the sensitivity of the assay, and so optimise the utility of preparations of GAD for diagnostic tests on serum for autoimmune insulin-dependent diabetes mellitus.

There is prior recognition that dimeric and multimeric forms of the GAD exist naturally in the body, and it has been reported that such dimeric and multimeric forms, stabilised by chemical procedures, can react with the autoantibodies present in serum of persons with diabetes[25]. However, the standard methods of detecting this serum reactivity, which are carried out in the presence of reducing agents that break disulphide bonds and/or electrostatic or hydrophobic interactions, result in the destruction of dimers and oligomers that are not completely stabilised. Hence, monomeric GAD has been considered hitherto as the major autoantigenic form of GAD.

As noted above, the essential characteristics of the diagnostic assay for autoantibodies to GAD in accordance with the present invention are the use of an antigen preparation containing an enhanced amount of dimeric or oligomeric GAD instead of monomeric GAD, together with appropriate reaction conditions which avoid the destruction of the dimers or oligomers.

In the work leading to the present invention, two separate preparations of GAD derived by entirely different procedures were tested, and with each the reactivity of sera from patients with IDDM is only with GAD in its dimeric/oligomeric form. Thus there is solid evidence that the major pancreatic islet autoantigen in IDDM, exists not as hitherto believed as a reactant of 64 kD but rather a s a reactant of 120–130 kD (and greater) GAD, interpretable as a dimeric/oligomeric form of the molecule. Overall, the results set out in Examples 1–8 below establish clearly that GAD is required to be in this dimeric or oligomeric form to be reactive with the autoantibody to GAD in IDDM sera. It therefore follows that any procedure that enhances the amount of dimeric or oligomeric GAD in a GAD preparation would generate an antigenic preparation that would bind even more strongly and more specifically with anti-GAD present in IDDM sera compared with preparations used hitherto. This in turn provides to a more sensitive assay with greatly improved diagnostic utility.

Enrichment of the dimeric/oligomeric fraction of GAD can be achieved by a number of methods obvious to one skilled in the art of protein biology. These procedures include the purification of the dimeric/oligomeric forms of GAD which can be accomplished by a number of methods including gel filtration, HPLC, affinity chromatography, ion exchange chromatography, etc. The enrichment may also be achieved by the classical cross-linking of monomeric GAD using hetero-bi functional or homo-bi functional reagents known to form co-valent intra-molecular and inter-molecular protein-protein associations.

Apart from the essential characteristic of use of an antigen preparation containing an enhanced amount of dimeric or oligomeric GAD 65 and/or GAD 67, the assays of the present invention can be performed using conventional protocols for immunoassays, such as competitive immunoassays, radio-immunoassays, enzyme-linked immunosorbent assays, and the like. Further details of suitable assay protocols in accordance with this invention are described, by way of example, in International Patent Specification No. PCT/US91/06438 (WO 92/04632), the disclosure of which is incorporated herein by reference.

The present description of the invention shows that IDDM sera react preferentially with dimeric or oligomeric forms of molecular GAD. Hence any method or procedure that provides a preparation in which the amounts or proportions of dimeric/oligomeric GAD are enhanced would create a more effective reactant for the serological diagnosis of IDDM. Such methods for the isolation of GAD include both chemical methods and immunochemical separations such as affinity chromatographic procedures that may be modified to give higher yields of dimers. Similarly, methods or procedures that resulted in the creation and stabilisation from monomeric GAD (recombinant or naturally occurring) of dimeric or oligomeric molecules by appropriate cross-linking, or formation of disulphide bonds, or other means, will yield a preparation containing dimeric GAD with an enhanced capacity to react with IDDM sera.

In this context, the GAD molecule in the dimeric form may acquire the appropriate "folding" to create the epitope that is optimally reactive with IDDM sera. There exist enzymes that react with proteins to produce molecules that are appropriately folded for optimal cellular transport and function, of which one example is protein disulphide isomerase (PDI). GAD in its monomeric form, either as a recombinant molecule or as native monomer, may be susceptible to the folding influences of enzymes such as PDI, so creating an enhanced reactant with IDDM serum. It is further to be noted that both homodimers and heterodimers of GAD 65 and GAD 67 may be prepared, and that the preparation of heterodimers of GAD 65-GAD 67 may provide a reactant of particular utility for serological testing.

Further details of the present invention will be apparent from the following Examples and the drawings which are included by way of illustration, not by way of limitation, of this invention.

EXAMPLE 1

This Example demonstrates that autoantibodies in sera from patients with IDDM react with dimeric/oligomeric forms of porcine brain GAD as shown by autoradiography of immunoprecipitates in SDS-polyacrylamide gels.

The nature of the GAD antigen reacting in the radioimmunoprecipitation assay described by Rowley et al. 6 was investigated as follows. The pellet consisting of antigen and antibody that was deposited after immunoprecipitation with Sepharose-protein A was exposed to polyacrylamide gel electrophoresis in the presence of sodium dodecyl sulphate (SDS-PAGE), and the gel was examined by autoradiography. The $^{125}$I-GAD antigen in the precipitate was compared with the GAD labelled with $^{125}$I that had been initially added to the assay.

For electrophoresis, samples were dissolved in a buffer that contained 64 mM Tris-HCl, pH 6.8, 2% SDS, and 10% glycerol with or without 5% 2-mercapto-ethanol. Electrophoresis was performed on 10% separating gels. The gels were dried and examined by autoradiography for periods of up to 2 weeks.

Figure 1:
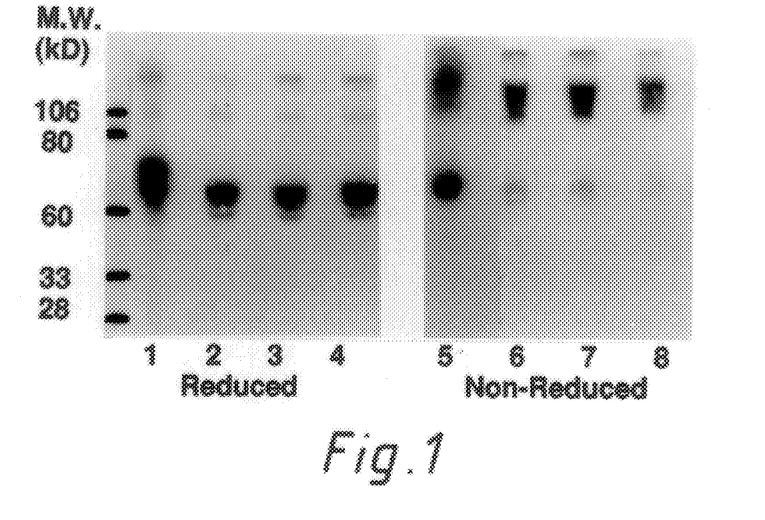
FIG. 1 shows the results by autoradiography of $^{125}$I-GAD that was precipitated with three representative IDDM sera and analysed by SDS-PAGE under reducing or non-reducing conditions (see text). Lanes 1 and 5 contain non-immunoprecipitated $^{125}$I-GAD and lanes 2, 3, 4 and 6, 7 8 contain $^{125}$I-GAD precipitated with three representative sera from patients with IDDM. It is clearly seen that under reducing conditions there is a strong signal at ~64 kD, and weak signals at 110–130 kD, whereas under non-reducing conditions there is a weak signal at 64 kD and a strong signal at 110–130 kD.

Typical results obtained from autoradiography are shown in FIG. 1. $^{125}$I-GAD was immunoprecipitated with the IDDM serum and the precipitate was analysed by gel electrophoresis with or without the reducing agent, 2-mercaptoethanol, i.e. reducing or non-reducing conditions. The gel was exposed for autoradiography for 2 weeks. In the Figure, lanes 1 and 5 contain non-immunoprecipitated $^{125}$I-GAD and lanes 2, 3, 4 and 6, 7, 8 contain $^{125}$I-GAD precipitated with three representative sera from patients with IDDM. Under reducing conditions (lanes 1–4), the non-precipitated GAD and the immunoprecipitated GAD have a similar migration corresponding to a MW of ~64 kD. However, under non-reducing conditions (lanes 5–8), the non-precipitated GAD appears as two components that have a migration corresponding to MW of ~64 kD and ~110–130 kD, whereas the precipitated GAD has a migration exclusively as a component corresponding to a MW of ~110–130 kD.

For the immunoprecipitates from sera that gave a positive result for antibodies to GAD, the period required for autoradiography to give a clear signal was 1–2 weeks. Under reducing conditions, i.e. in the presence of 2-mercaptoethanol, the iodinated protein that was precipitated by IDDM sera that contained antibodies to GAD had a molecular weight of ~64 kD. Under non-reducing conditions in which the molecular configuration of dimers and oligomers is not altered, only negligible amounts of iodinated protein with a molecular weight of ~64 kD were precipitated, whereas there was a strong signal that corresponded to an iodinated protein(s) with a molecular weight of ~110–130 kD, together with a weaker signal that corresponded to components of molecular weight greater than 200 kD, presumably oligomeric aggregates of the ~64 kD material. On the other hand, when the same $^{125}$I-GAD preparation that had been added to the immunoprecipitation mixture was examined directly using electrophoresis under either reducing or non-reducing conditions, there was a strong signal corresponding to the presence of an iodinated protein of molecular weight ~64 kD.

EXAMPLE 2

This Example demonstrates that diabetic sera immunoprecipitate only a small fraction of the total amount of iodinated GAD in a test preparation of affinity-purified porcine brain GAD, irrespective of the amount or potency of serum used for the immunoprecipitation.

Figure 2:
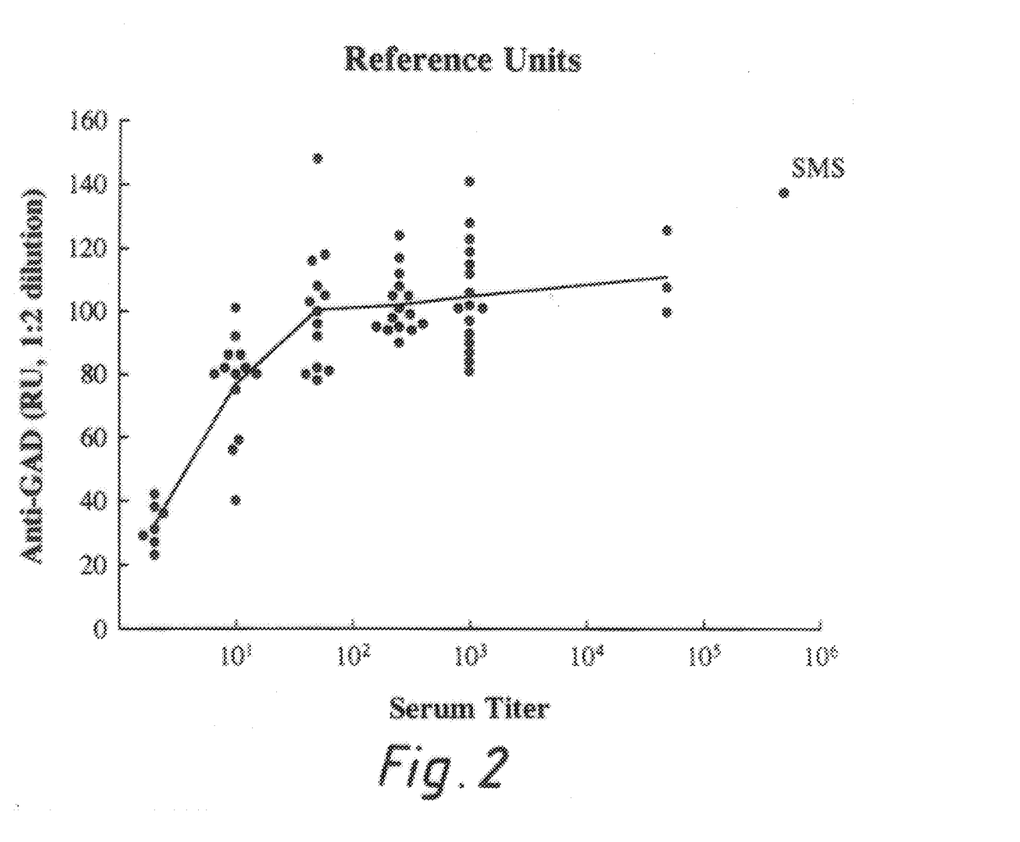
FIG. 2 shows end-point titrations for 68 IDDM sera, including one with Stiff Man Syndrome (SMS), plotted against the value in reference units for the same sera at a 1:2 dilution. Note that a plot of mean values reaches a plateau corresponding to 5–10% of the total GAD added, indicating that not all of the GAD in the preparation can be precipitated, even with high potency sera, as judged by high titre.

In an affinity purified preparation of porcine brain GAD, only a small fraction is in an appropriate autoantigenic configuration for reactivity with IDDM serum, as shown by the consistently repeated finding that it is not possible to immunoprecipitate more than 5–10% of the total $^{125}$I-GAD in the radio-immunoprecipitation assay (observed on more than 1000 IDDM sera tested in the present inventors' laboratory). In fact, the total amount of radioiodine-labelled porcine brain GAD immunoprecipitated by any IDDM serum reaches a plateau at a level corresponding to only 5–10% of the total counts of radioactivity added, with no increase obtained by the addition of further amounts of IDDM serum (FIG. 2). Moreover, when IDDM sera that give a positive reaction in the radioimmunoprecipitation assay are titrated from the usual 1:2 initial dilution, it is evident that the end-point titration is in many cases beyond a serum dilution of 1:1000 (FIG. 2), indicating that the failure to immunoprecipitate most of the $^{125}$I-GAD in the preparation is not due to any lack of potency in the precipitating antisera.

EXAMPLE 3

This Example shows that the removal of the dimeric and oligomeric forms of GAD from the GAD preparations abrogates reactivity of IDDM sera with GAD.

In the radioimmunoprecipitation assay, the residual supernatant after immunoprecipitation of $^{125}$I-GAD by IDDM serum regularly contains most of the initial radioactivity added (see above). Autoradiography of the residual $^{125}$I-GAD after electrophoresis shows a signal corresponding to a ~64 kD component, this being precisely comparable with the ~64 kD signal in the original GAD preparation. There are, however, now no other signals corresponding to components of higher molecular weights, these components having been completely removed by the first immunoprecipiation.

Experiments were performed to determine the degree to which removal of the dimeric/oligomeric forms of GAD from the initial preparation of $^{125}$I-GAD would remove the capacity to react with IDDM sera. Accordingly, the $^{125}$I-GAD preparation was allowed to react (i.e. absorbed) at 40° C. overnight either with a strongly positive IDDM serum, or with pooled normal sera, then immunoprecipitation was performed with protein A-Sepharose to remove all immune complexes of $^{125}$I-GAD-anti-GAD. The absorbed supernatant was then used as antigen in the standard immunoprecipitation assay using either IDDM sera or normal human sera. The result was that the supernatant derived after immunoprecipitation (absorption) with a strongly positive IDDM serum generally failed to function as an antigen in the standard radioimmunoprecipitation assay. (There were, however, three anomalous exceptions, discussed in Example 4.) The typical results are shown in Table 1. It should be noted that after the initial precipitation (absorption) of $^{125}$I-GAD with IDDM serum, further precipitation with IDDM serum immunoprecipitated no more radioactivity than could be precipitated with a normal serum. On the other hand, after an initial precipitation (absorption) with a normal serum, the number of counts of radioactivity that could be precipitated from the $^{125}$I-GAD preparation by an IDDM serum was precisely equivalent to the number of counts of radioactivity precipitated using a fresh non-absorbed preparation of $^{125}$I-GAD tested under exactly the same conditions.

TABLE 1

| | Second Precipitation (cpm) | |
|---|---|---|
| Initial Precipitation | IDDM serum | Normal serum |
| IDDM serum | 390 | 252 |
| Normal serum | 2400 | 97 |
| Nil* | 2600 | 78 |

*Counts precipitated with fresh $^{125}$I-GAD using the same volume of the autoantigen GAD (130 μl) and the same number of initial counts (38,000 cpm) as were used with the supernatant after absorption.

In this Example an initial precipitation of $^{125}$I-GAD was made either with IDDM serum or normal serum, with a second precipitation likewise, with results compared with those with no initial precipitation (Nil). The results show that the initial precipitation with the IDDM serum removed the reactive capacity of the GAD whereas after initial precipitation with normal serum the reactive capacity of the GAD for IDDM serum was unchanged.

EXAMPLE 4

This Example shows that very exceptional sera from cases of IDDM do react with a monomeric form of purified brain GAD. The identification and characterisation of these anomalously-reactive sera does not derogate from the importance of the dimeric and oligomeric forms of GAD in diagnosis of IDDM. Indeed, the highly exceptional immunoprecipitation reactivity of these sera with GAD in the monomeric rather than dimeric or oligomeric forms provides strong validation of the data herein that in the immunoprecipitation assay, IDDM sera react usually and typically with GAD in the dimeric/oligomeric conformation.

As demonstrated above, for most IDDM sera, the radioimmunoprecipitation assay with $^{125}$I-GAD is carried out under conditions of antibody excess, such that these sera remain reactive at dilutions of 1:100 or 1:1000 or even higher, yet most IDDM sera react with only ~5–10% of the total iodinated GAD in the preparation.

However, although this is the pattern of reactivity observed for the overwhelming majority of IDDM sera tested, in fact well over 99%, an anomalous pattern of reactivity has been observed with three sera. Each of these three sera precipitated more than 10% and up to 30% of the total iodinated GAD in the standard immunoprecipitation assay at a 1:2 dilution. Nonetheless, and despite the apparent potency of these three sera, in each case the reactivity in the immunoprecipitation assay decreased rapidly after dilution of the serum, and thus the potency according to titration was actually low.

Figure 3:
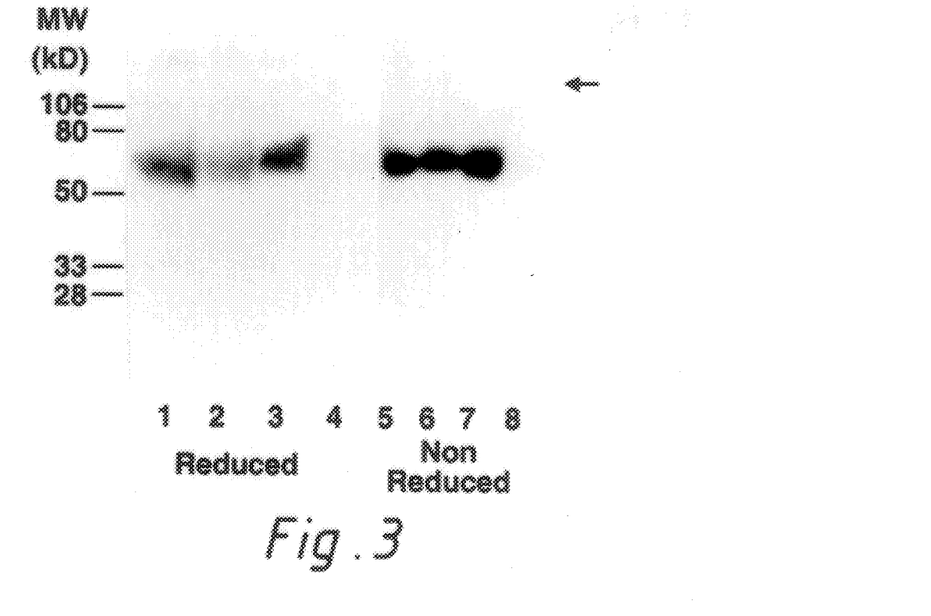
FIG. 3 shows the results by autoradiography of $^{125}$I-GAD that was precipitated with three anomalous sera and analysed by SDS-PAGE under reducing and non-reducing conditions. Here, and in the particular contrast to FIG. 1, the precipitated $^{125}$I-GAD migrates only as a ~64 kD component. Lanes 1–3 and 5–7 are the anomalous sera. Lanes 4 and 8 are a typical IDDM serum. The typical IDDM serum (lane 8) has reactivity, as expected, only with the 110–130 kD component under non-reducing conditions, with a weak signal at the exposure time used for this autoradiograph (arrow).

Immunoprecipitation followed by autoradiography under non-reducing conditions, as described above, was applied to detect whether these sera were reacting with dimer/oligomer. The result was that pellets obtained from immunoprecipitation with these three anomalous sera showed a strong reactivity with a component corresponding in MW to monomeric GAD but no apparent reactivity with the dimer/oligomeric forms of GAD (FIG. 3).

In order to determine whether removal of dimeric/oligomeric forms of GAD from the preparation would affect the reactivity of these anomalous sera, the immunoprecipitation was repeated using as the source of $^{125}$I-GAD the supernatant obtained after an initial immunoprecipitation (i.e. absorption) with an IDDM serum as described above (see Example 3). In this experiment an initial absorption of the $^{125}$I-GAD preparation with an IDDM serum did not remove the reactivity of the $^{125}$I-GAD with these three sera although, as expected, and as previously shown, it did significantly reduce the reactivity with all typically reactive IDDM sera. The results of this experiment are shown in Table 2.

TABLE 2

| | Second Precipitation (cpm) | | | |
| --- | --- | --- | --- | --- |
| | Atypical Sera | | | |
| Initial Precipitation | Serum 1 | Serum 2 | Serum 3 | IDDM serum |
| IDDM serum | 12,500 | 8,756 | 12,580 | 2,400 |
| Nil | 13,100 | 6,600 | 7,800 | 4,800 |

In this Example, the results after an initial precipitation of GAD with IDDM serum or no serum (nil) are shown for three anomalous sera that did react with monomeric GAD. For these sera the reactive capacity was retained after the initial precipitation. Note that in contrast the reactive capacity of the GAD for a typical IDDM serum was significantly reduced after the initial precipitation.

EXAMPLE 5

This Example shows that the dimeric/oligomeric forms of GAD that contain both GAD 65 and GAD 67 react with sera from patients with IDDM.

GAD preparations derived from porcine brain contain both GAD 65 and GAD 67. This indicates that there would be a substantial amount of the heterodimeric form of GAD, GAD 65-GAD 67 in a porcine brain GAD preparation, given that the monoclonal antibody GAD 1 that is used in the affinity purification is reported to react with only GAD 65. Thus GAD 67 could become bound to the affinity column only through its linkage to GAD 65.

Evidence that a heterodimer of GAD 65 and GAD 67 is reactive with sera from patients with IDDM is available from immunoprecipitation studies in which the antigenic material was the supernatant obtained after initially performing the immunoprecipitation assay using either the monoclonal antibody GAD 6 that reacts with GAD 65[19], or using the polyclonal antibody K2 raised in the rabbit that is stated to react only with GAD 67[26]. The results are shown in Table 3. After initial precipitation was performed with K2 to remove GAD 67, the reactivity of IDDM sera with the supernatant was reduced from 2600 cpm obtained without any initial immunoprecipitation, to 1300 cpm, i.e. about 50%. By contrast, after an initial precipitation with the monoclonal antibody GAD 6 that reacts with GAD 65, or with an initial immunoprecipitation with a potent IDDM serum, there was a reduction of the reactivity by virtually 100%, i.e. to the level observed using serum from healthy blood donors.

TABLE 3

| | Second Precipitation (cpm) | |
| --- | --- | --- |
| Initial Precipitation | IDDM serum | Normal Serum |
| GAD 6 | 197 | 232 |
| K2 | 1296 | 230 |
| IDDM serum | 390 | 252 |
| Normal serum | 2427 | 97 |
| Nil | 2590 | 78 |

In this Example, an initial precipitation of a GAD preparation was made with various reactants, the monoclonal antibody GAD 6 against GAD 65, the polyclonal rabbit antibody K2 against GAD 67, IDDM serum or normal serum, and followed by a second precipitation with an IDDM serum or normal serum. The results show that the capacity of GAD to react with IDDM serum was moderately influenced by serum K2 and markedly by GAD 6 and the IDDM serum. From the finding that GAD 6 and K2 are totally depleting, the inference is that homodimers and heterodimers of GAD 65/GAD 67 are present in the GAD preparation and both homo- and heterodimeres are reactive.

EXAMPLE 6

This Example shows that denaturation of the autoantigenic protein GAD influences its reactivity with IDDM sera.

"Western" transfer immunoblotting is a standard procedure for examining the reactivity of autoimmune sera with protein components, including intracellular proteins. This procedure is usually performed under conditions in which the antigenic protein is denatured by exposure to heat (boiling), a reducing agent (2-mercaptoethanol) and the detergent sodium dodecyl sulphate (SDS). The polypeptide epitopes so defined are therefore regarded as "linear" rather than "conformational", although some degree of renaturation may occur after transfer of the proteins from the gel to the nitrocellulose filter.

Figure 4:
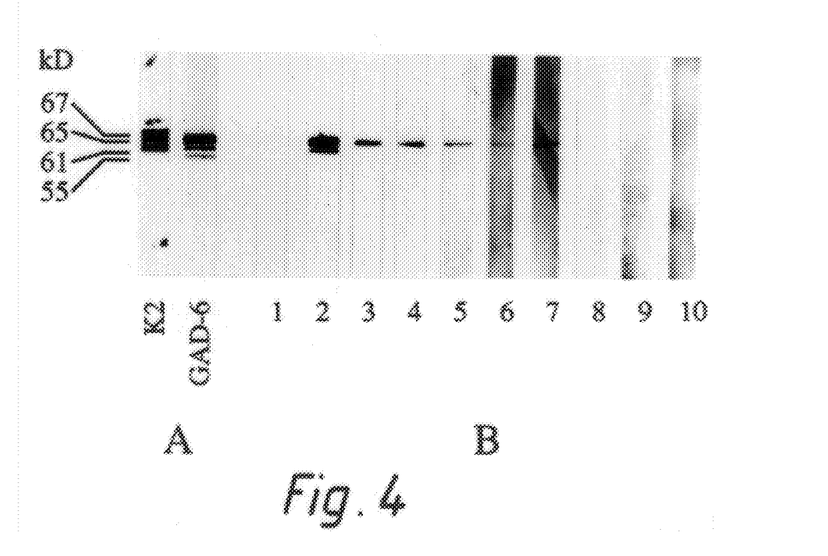
FIG. 4 shows the result by Western blotting after SDS-PAGE electrophoresis of GAD using antibodies to GAD raised experimentally (A) and in humans (B), with serum dilutions of 1:200. (A) Monoclonal mouse antibody GAD-6 raised against GAD 65, and polyclonal rabbit antibody K2 raised against GAD 67; (B) lane 1, healthy person; lane 2, patient with SDS and IDDM; lanes 3–10, patients with IDDM.
Figure 5:
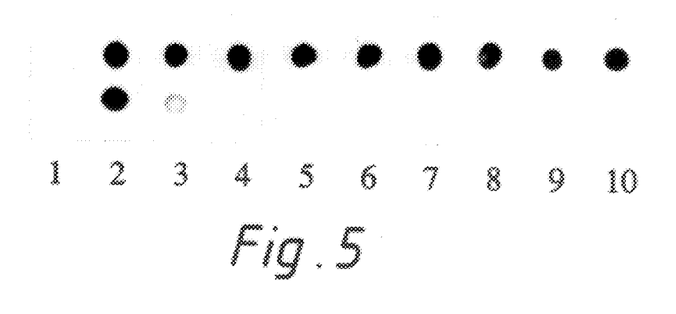
FIG. 5 shows the results by dot blotting whereby GAD is spotted onto a nitrocellulose filter and then exposed to the test sera. The upper row (spots 2–10) shows the reaction of IDDM sera with GAD under non-denaturing conditions (see text), wherein all sera show strong reactivity, and in contrast, the lower row (spots 2–10) shows the reaction of the same IDDM sera with GAD treated with ME and boiling wherein only serum 2, and serum 3 (weak) show reactivity. Spot 1 represents normal serum. The sera depicted here are the same as those depicted in FIG. 4.

Sera from patients with IDDM react with preparations of GAD by Western blotting with a component corresponding to a MW of 64–65 kD; however in fact only a small proportion (~10%) of IDDM sera actually do so according to the experience of the present inventors[27] and that of other[5,28,29] (FIG. 4). This would indicate that IDDM sera usually react with a conformational epitope structure associated with the GAD molecule that is lost under the usual conditions of immunoblotting. Consistent with this is the finding that IDDM sera usually do react with the GAD molecule when this is "spotted" onto a nitrocellulose filter as a dot blot under non-denaturing conditions, these being the absence of 2-mercaptoethanol, heating and sodium dodecyl sulphate[27] (FIG. 5). However, since the dot blotting procedure does not involve the molecular separation in gels of the reacting protein, there can be no information on the molecular weight of the GAD reactant in the dot blotting procedure. In the dot blotting system, it was found that 2-mercaptoethanol did not interfere with reactivity, whereas boiling of the GAD preparation abrogated its reactivity with IDDM sera.

As described above, autoradiography of immunoprecipitated pellets (GAD-anti-GAD) after gel electrophoresis exposed to sodium dodecyl sulphate and boiling, but in the absence of 2-mercaptoethanol, shows a component corresponding in molecular weight to a dimeric form of GAD (~120 kD). It was ascertained that exposure to mild heating, 60° C. for 2 minutes, resulted in a loss of the capacity of $^{125}$I-GAD to react with IDDM sera, whereas exposure to 2-mercaptoethanol did not result in loss of capacity to react with IDDM sera. Autoradiography under non-reducing conditions of the immunoprecipitated pellets after the $^{125}$I-GAD had been treated with 2-mercaptoethanol before use in the immunoprecipitation assay showed that there was retention of the dimeric structure, indicating that the molecule in its dimeric configuration appears to be resistant to reduction in the absence of heating.

It is noted in relation to the results from Western blotting and gel analyses of immunoprecipitates using affinity purified porcine brain GAD, that in the Western blotting procedure the antigen is exposed to denaturing conditions before the reaction with serum antibody, whereas with gel analyses of immunoprecipitates, the exposure to denaturing conditions is after the formation of the antigen-antibody complex.

These results indicate that the reactive epitope presented by the GAD molecule is sensitive to conditions that interfere with the conformational structure of proteins, and are consistent with this epitope being a construct of GAD molecules in a dimeric or oligomeric configuration.

EXAMPLE 7

This Example shows that recombinant GAD produced in a bacterial expression system is inactive in the immunoprecipitation assay, although the recombinant protein has strong enzymatic activity, and hence must retain most of the native configuration of the molecule.

The action of an enzyme is highly dependent on the conformational structure of the molecule since the activity of most enzymes is readily destroyed when the conformational structure is lost, and GAD is completely inactivated by heating for 2 hours at 45° C.[20]. Accordingly, an enzymatically active molecule is usually considered to exist folded in its native conformation[30].

Recombinant GAD 65 was prepared in the bacterial expression system pMAL (New England Biolabs)[31]. The recombinant protein was shown to have strong enzymatic activity as measured by the production of GABA from glutamate labelled with $^3$H, according to the procedure described by Rowley et al.[6], and the specific activity of the recombinant protein was much greater than the specific activity of the purified porcine brain GAD. Nonetheless, when the recombinant GAD antigen was labelled with $^{125}$I and used as antigen in the standard immunoprecipitation assay, it proved to be poorly reactive.

Recombinant GAD has been used previously with some claimed success in ELISA systems, but the performance of such ELISAs using recombinant GAD is quite inferior to the performance of radioimmunoprecipitation assays using native porcine brain GAD, as judged by published results[32] and results from the First International GAD Antibody Workshop[33].

Thus, the conformational requirement of the GAD molecule for reactivity with sera from patients with IDDM differs from the conformational requirement for enzymatic activity, indicating that the additional conformational requirement for immunoprecipitation is critically dependent on a dimeric/oligomeric configuration of the GAD molecule.

EXAMPLE 8

In this Example, the use of recombinant GAD derived from a rabbit reticulocyte lysate establishes that a dimeric-oligomeric form of the molecule carries the antigenic reactivity.

Each of the experiments described in Examples 1–6 was carried out using GAD prepared by immunochemical means from porcine brain. It might be assumed that some of the GAD in the preparation becomes damaged during the extraction process, and that the dimeric or oligomeric structure of the molecule is protective of the antigenicity of the naturally occurring GAD. On this assumption, the exclusive reactivity of IDDM sera with dimeric or oligomeric GAD could represent an artefact of the preparation method. In that case, monomeric GAD prepared by other methods should react with IDDM sera.

It is now established in various laboratories that recombinant GAD produced in different eukaryotic expression systems can be successfully used to assay for antibodies to GAD[29,34,35]. If there were an absolute requirement for reactivity that IDDM sera engage a dimeric/oligomeric form of GAD, then with GAD derived from these expression systems the material immunoprecipitated by sera from patients with IDDM should, as for native brain GAD, be in a dimer/oligomer configuration.

Figure 6:
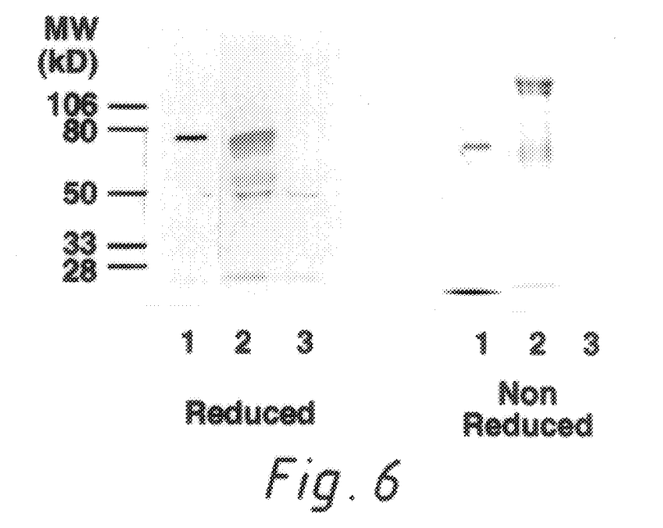
FIG. 6 shows the results by autoradiography of biosynthetically labelled recombinant GAD($^{35}$S-GAD) prepared so as to retain the normal structure of native GAD by expression using rabbit reticulocyte lysate (RRL); precipitation was with a representative positive IDDM serum and a negative serum, and analysed by SDS-PAGE under reducing and non-reducing conditions. In each case, lane 1 contains the RRL recombinant GAD (19 hour exposure), lane 2 contains RRL-expressed GAD precipitated with IDDM serum (7 day exposure), and lane 3 contains RRL-expressed GAD precipitated with a normal serum (7 day exposure). Note that with precipitated RRL-expressed GAD analysed under non-reducing conditions the major signal corresponds to a M.W. of 110–130 kD, indicative of a dimeric form of GAD.

The above presumption was tested as follows. Recombinant GAD biosynthetically labelled with $^{35}$S-methionine was prepared using in vitro transcription with SP6 polymerase, followed by in vitro translation using rabbit reticulocyte lysate[36]. The biosynthetically labelled $^{35}$S-GAD was analysed by SDS-PAGE under reducing conditions, followed by autoradiography, and shown to be very pure, consisting almost exclusively of a single protein component with a molecular weight of ~64 kD (FIG. 6).

This purified, eukaryotically expressed $^{35}$S-GAD was used as an antigen in the immunoprecipitation assay with IDDM and normal sera as described previously. The result was that, as for affinity purified brain GAD, only a small proportion of the total radioactivity could be immunoprecipitated. The immunoprecipitated pellet (GAD-anti-GAD) was examined by autoradiography after separation of proteins by electrophoresis under non-reducing conditions and, as previously, only the dimeric form of GAD was immunoprecipitated. It is important to note that most of the $^{35}$S-GAD in the preparation was in the monomeric form, yet this major proportion proved to be non-precipitable.

REFERENCES:

1. World Health Organization: *Diabetes Mellitus; Report of WHO Study Group.*, Geneva, World Health Org., (1985). Tech.Rep.Ser.No.727.
2. Ziegler, A. G., Herskowitz, R. D., Jackson, R. A., Soeldner, J. S., Eisenbarth, G. S. Predicting type I diabetes. *Diabetes Care* 13:762–75, (1990).
3. Baekkeskov, S., Nielsen, J. H., Marner, B., Bilde, T., Ludvigsson, J., Lemark, A. Autoantibodies in newly diagnosed diabetic children immunoprecipitate human pancreatic islet cell proteins. *Nature* (Lond.) 298: 167–69, (1982).
4. Atkinson, M. A., Maclaren, N. K., Scharp, D. W., Lacy, P. E., Riley, W. J. 64,000$M_r$ autoantibodies as predictors of insulin-dependent diabetes. *Lancet* 335:1357–60, (1990).
5. Baekkeskov, S., Aanstoot, H-J., Christgau, S., Reetz, A., Solimena, M., Cascalhom, Holli, F., Ritcher Olesen, H., DeCamilli, P. Identification of the 64 K autoantigen in insulin-diabetes as the GABA-synthesizing enzyme glutamic acid decarboxylase. *Nature* (Lond.) 347:151–56, (1990).
6. Rowley, M. J., Mackay, I. R., Chen, Q-Y, Knowles, W. J., Zimmet, P. Z. Antibodies to glutamic acid decarboxylase discriminate major types of diabetes mellitus. *Diabetes* 41:548–51, (1992).
7. Maclaren, N. K., Schatz, D. S., Drash, A., Graves, G. Initial pathogenic events in IDDM. *Diabetes* 38:534–38, (1988).
8. Bottazzo, G. F., Florin-Christensen, A., Doniach, D. Islet cell antibodies in diabetes mellitus with autoimmune polyendocrine deficiencies. *Lancet* 2:1279–83, (1974).
9. Palmer, J. P., Asplin, C. M., Clemons, P., Lyen, K., Tarpati, O., Raghu, P. K., Paguette, T. L. Insulin antibodies in insulin-dependent diabetes before insulin treatment. *Science* 222:1337–39, (1983).
10. Czarnocka, B., Ruf, J., Ferrand, M., Carayon, P., Lissitzky, S. Purification of the human thyroid peroxidase and its identification as the microsomal antigen involved in autoimmune thyroid disease. *FEBS Lett.* 190:147–52, (1985).

11. Gleeson, P. A., Toh, B-H. Molecular targets in pernicious anaemia. *Immunol. Today,* 12:233–39, (1991).
12. Gershwin, M. E., Mackay, I. R. Primary biliary cirrhosis; paradigm or paradox for autoimmunity. *Gastroenterology* 100:822–23, (1991).
13. Cram, D. S., Barnett, L. D., Joseph, J. L., Harrison, L. C. Cloning and partial nucleotide sequence of human glutamic acid decarboxylase (GAD) cDNA from brain and pancreatic islets. *Biochem. Biophys.Res.Commun.* 176:1239–44, (1991).
14. Wyborski, R. J., Bond, R. W., Gottlieb, D. I. Characterization of a cDNA coding for rat glutamic acid decarboxylase. *Mol.Brain Res.* 8:193–98, (1990).
15. Kobayashi, Y., Kaufman, D. L., Tobin, A. J. Glutamic acid decarboxylase cDNA; nucleotide sequence encoding an enzymatically active fusion protein. *J.Neurosci.* 7:2768–72, (1987).
16. Karlsen, A. E., Hagoplan, W. A., Grubin, C. E., Dube, S., Disteche, C. M., Adler, D. A., Barmeler, H., Mathewes, S., Grant, F. J., Foster, D., Lernark, A. Cloning and primary structure of a human isoform of glutamic acid decarboxylase from chromosome 10. *Proc. Natl. Acad. Sci. (USA).* 88:8837–41, (1991).
17. Michelson, B. K., Petersen, J. S., Boel, E., Moldrup, A., Dyrberg, T., Madsen, O. D. Cloning, characterization, and autoimmune recognition of rat islet glutamic acid decarboxylase in insulin-dependent diabetes mellitus. *Proc. Natl. Acad. Sci. (USA).* 88:8754–58, (1991).
18. Kaufman, D. I., McGinnis, J. F., Krieger, N. R., Tobin, A. J. Brain glutamate decarboxylase cloned in γ-arninobutyric acid. *Science*232:1138–40, (1986).
19. Chang, Y. C., Gottleib, D. I.. Characterization of the proteins purified with monoclonal antibodies to glutamic acid decarboxylase. *J.Neurosci.* 8:2123–30, (1988).
20. Nathan, B., Bao, J., Hsu, C-C, Aguilar, P., Wu, R., Yaram, M., Kuo, C-Y., Wu-, J-W. A membrane form of brain 1-glutamate decarboxylase: identification, isolation, and its relation to insulin-dependent diabetes mellitus. *Proc. Natl. Acad. Sci. (USA)* 91:242–246.
21. Tuomi, T., Zimmet, P. Z., Rowley, M. J., Serjeantson, S. W., Mackay, I. R. Persisting antibodies to glutamic acid decarboxylase in Type I (insulin-dependent) diabetes mellitus are not associated with neuropathy. *Deabetologia* 36:685.
22. Zimmet, P. Z., Elliott, R. R., Mackay, I. R., Tuomi, T., Rowley, M. J., Pilcher, C. C., Knowles, W. J. Autoantibodies to glutamic acid decarboxylase and insulin in presymptomatic type I (insulin-dependent) diabetes mellitus: frequency and segregation by age (submitted).
23. Tuomilehto, J., Zimmet, P., Mackay, I., Koskela, P., Widgren, G., Toivanen, L., Tuomilehto-Wolf, E., Kohtamaki, K., Stengard, J., Rowley, M. Antibodies to glutamic acid decarboxylase are strong predictors of insulin-dependenit diabetes mellitus before the clinical onset of the disease (submitted).
24. Beischer, N. A., Wein, P., Mackay, I. R., Rowley, M. J., Zimmet, P., Colman, P. G., Sheedy, M. Prevalence of glutamic acid decarboxylase antibody and islet cell antibody in women who have had gestational diabetes including 19 who now have insulin-requiring diabetes (submitted).
25. Petersen, J. S., Hejnaes, K. R., Baekkeskov, S. Characterization of the oligomerization of glutamate decarboxylase. (Abstract). *Diabetes* 41:38A (1992).
26. Kaufmann, D. L., Houser, C. R., Tobin, A. J.. Two forms of the γ-aminobutyric acid synthetic enzyme glutamate decarboxylase have distinct intraneuronal distributions and cofactor interactions. *J. Neurpmchem.* 56:720–723 (1991).
27. Tuomi, T., Rowley, M.J., Knowles, W., McAnally, T., Chen, Q-Y., Zimmet, P. Z., Mackay, I. R. Autoantigenic properties of native and denatured glutamic acid decarboxylase: evidence for a conformational epitope. *Clin. Immunol. Immunopathol.* (in press).
28. Tuck, A. B., Petley, A. M., Wilkin, T. J. Failure to detect autoantibodies specific for IDDM by Western blotting. *Autoimmunity* 13:173–174.
29. Karlsen, A. E., Hagopian, W. A., Petersen, J. S., Boel, E., Dyrberg, T., Grubion, C.E., Michelsen, B.K., Madsen, O.D., Lernmark, A. Recombinant glutamic acid decarboxylase (representing the single isoform expressed in human islets) detects IDDM-associated 64,000-$M_r$ autoantibodies. *Diabetes* 41: 1355–59 (1992).
30. Laver, W. G., Air, G. M., Webster, R. G., Smith-Gill, S. J. Epitopes on protein antigens: misconceptions and realities. *Cell* 61:553–556 (1990).
31. Guan, C., Li, P., Riggs, P. D., Inouye, H. Vectors that facilitate the expression and purification of foreign peptides in *Escherichia coli* by fusion to maltose-binding protein. *Gene* 67:21–30 (1987).
32. DeAizpurua, H. J., Harrison, L. C., Cram, D. S. An ELISA for antibodies to recombinant glutamic acid decarboxylase in IDDM. *Diabetes* 41:1182–1187 (1992).
33. Schmidli, R. S., Colman, P. G., Bonifacio, E., Boltazzo, G. F., Harrison, L. C. and participation laboratories. High level of concordance between assays for glutamic acid decarboxylase antibodies (GAD Ab): the First International GAD Ab workshop. *Diabetes*, (submitted).
34. Seissler, J., Amann, J., Maunch, L., Haaubruck, H., Wolahrt, S., Bieg, S., Richter, W., Holl, R., Heinze, E., Northemann, W., Scherbaum, W.A. Prevalence of autoantibodies to the 65- and 67-kD isoforms of glutamate decarboxylase in insulin-dependent diabetes mellitus. *J.Clin. Invest.* 92:1394–1399 (1993).
35. Hagopian, W. A., Michelsen, B., Karksen, A. E., Larsen, F., Moody, A., Grubin, C. E., Fowe, R., Petersen, J., McEvoy, R., Lernmark, A. Autoantibodies in IDDM primarily recognize the 65,000-$M_r$ rather than the 67,000-$M_r$ isoform of glutamic acid decarboxylase. *Diabetes* 42:631–36 (1993).
36. Krieg, P. A., Melton, D. A. Functional messenger RNAs are produced by SP6 in vitro transcription of cloned cDNAs. *NucL. Acids Res.* 12:7057–7070 (1984).

We claim:

1. A method for detecting autoantibodies to glutamic acid decarboxylase (GAD) in the serum of a patient, comprising the steps of;

contacting a serum sample from the patient with a GAD preparation, and detecting the binding of GAD autoantibodies in said sample by said GAD preparation, wherein said GAD preparation comprises an enhanced amount of dimers or oligomers of the 65 kD isoform of GAD, the 67 kD isoform of GAD, or both, relative to preparations of naturally occurring GAD.

2. A method for diagnosing a diabetic or prediabetic condition in a patient, comprising the steps of:

detecting the presence of GAD autoantibodies in a serum sample from the patient by contacting said sample with a GAD preparation, wherein said GAD preparation comprises an enhanced amount of dimers or oligomers of the 65 kD isoform of GAD, the 67 kD isoform of GAD, or both, relative to preparations of naturally occurring GAD, wherein the presence of GAD autoantibodies in said sample is diagnostic of a diabetic or prediabetic condition in the patient.

3. A method according to claim 1, wherein said method is performed under conditions under which the dimeric or oligomeric form of GAD is retained.

4. A method according to claim 1, wherein said method is performed under non-denaturing conditions.

5. A method according to claim 1, wherein said method is performed under non-reducing conditions.

6. A method according to claim 1, wherein said GAD preparation comprises human or non-human mammalian, native or recombinant GAD selected from the group consisting of pancreatic GAD, brain GAD, and non-brain CNS GAD.

7. A method according to claim 1, wherein said GAD preparation comprises substantially pure GAD containing greater than 50% by weight of said dimeric or oligomeric forms of GAD.

8. A method according to claim 1, wherein said dimers or oligomers comprise heterodimers or heterooligomers of the 65 kD and 67 kD isoforms of GAD.

9. A method according to claim 2, wherein said method is performed under conditions under which the dimeric or oligomeric form of GAD is retained.

10. A method according to claim 2, wherein said GAD preparation comprises human or non-human mammalian, native or recombinant GAD selected from the group consisting of pancreatic GAD, brain GAD, and non-brain CNS GAD.

11. A method according to claim 2, wherein said GAD preparation comprises substantially pure GAD containing greater than 50% by weight of said dimeric or oligomeric forms of GAD.

12. A method according to claim 2, wherein said dimers or oligomers comprise heterodimers or heterooligomers of the 65 kD and 67 kD isoforms of GAD.

13. A method according to claim 2, wherein said method is performed under non-denaturing conditions.

14. A method according to claim 2, wherein said method is performed under non-reducing conditions.

15. A method according to claim 8, wherein said GAD preparation comprises at least 50% by weight of said heterodimers or heterooligomers of the 65 kD and 67 kD isoforms of GAD.

16. A method according to claim 12, wherein said GAD preparation comprises at least 50% by weight of said heterodimers or haterooligomers of the 65 kD and 67 kD isoforms of GAD.

17. A diagnostic kit for detecting autoantibodies to GAD in the serum of a patient, comprising:

a GAD preparation and means for detecting the binding of GAD autoantibodies in a serum sample from the patient by said GAD preparation, wherein said GAD preparation comprises an enhanced amount of dimers or oligomers of the 65 kD isoform of GAD, the 67 kD isoform of GAD, or both, relative to preparations of naturally occurring GAD.

18. A diagnostic kit according to claim 17, wherein said GAD preparation comprises human or non-human mammalian, native or recombinant GAD selected from the group consisting of pancreatic GAD, brain GAD, and non-brain CNS GAD.

19. A diagnostic kit according to claim 17, wherein said GAD preparation comprises substantially pure GAD containing greater than 50% by weight of said dimeric or oligomeric forms of GAD.

20. A diagnostic kit according to claim 17, wherein said dimers or oligomers comprise heterodimers or heterooligomers of the 65 kD and 67 kD isoforms of GAD.

21. A diagnostic kit according to claim 20, wherein said GAD preparation comprises at least 50% by weight of said heterodimers or heterooligomers of the 65 kD and 67 kD isoforms of GAD.

* * * * *